US010463606B2

(12) United States Patent
Frohberg et al.

(10) Patent No.: US 10,463,606 B2
(45) Date of Patent: *Nov. 5, 2019

(54) USE OF ALTERNAN AS TEXTURIZING AGENT IN FOODSTUFFS AND COSMETICS

(71) Applicant: BAYER INTELLECTUAL PROPERTY GMBH, Monheim am Rhein (DE)

(72) Inventors: Claus Frohberg, Kleinmachnow (DE); Jens Pilling, Dortmund (DE)

(73) Assignee: BAYER INTELLECTUAL PROPERTY GMBH, Monheim am Rhein (DE)

( * ) Notice: Subject to any disclaimer, the term of this patent is extended or adjusted under 35 U.S.C. 154(b) by 121 days.

This patent is subject to a terminal disclaimer.

(21) Appl. No.: 15/159,718

(22) Filed: May 19, 2016

(65) Prior Publication Data

US 2016/0278420 A1 Sep. 29, 2016

Related U.S. Application Data

(62) Division of application No. 12/921,046, filed as application No. PCT/EP2009/001760 on Mar. 6, 2009, now Pat. No. 9,370,203.

(60) Provisional application No. 61/068,894, filed on Mar. 11, 2008.

(30) Foreign Application Priority Data

Mar. 7, 2008 (EP) .................................... 08102410

(51) Int. Cl.
| *A61K 8/00* | (2006.01) |
| *A23D 7/005* | (2006.01) |
| *A61K 8/73* | (2006.01) |
| *A61Q 19/00* | (2006.01) |
| *A21D 2/18* | (2006.01) |
| *A61K 8/98* | (2006.01) |
| *A23C 9/137* | (2006.01) |
| *A23G 1/40* | (2006.01) |
| *A23G 3/42* | (2006.01) |
| *A23L 29/269* | (2016.01) |
| *A23L 7/117* | (2016.01) |
| *A23L 27/60* | (2016.01) |
| *A23L 33/20* | (2016.01) |
| *A23L 33/21* | (2016.01) |
| *A23L 33/115* | (2016.01) |

(52) U.S. Cl.
CPC ............... *A61K 8/986* (2013.01); *A21D 2/18* (2013.01); *A21D 2/183* (2013.01); *A23C 9/137* (2013.01); *A23D 7/005* (2013.01); *A23D 7/0053* (2013.01); *A23D 7/0056* (2013.01); *A23G 1/40* (2013.01); *A23G 3/42* (2013.01); *A23L 7/117* (2016.08); *A23L 27/60* (2016.08); *A23L 29/273* (2016.08); *A23L 33/115* (2016.08); *A23L 33/20* (2016.08); *A23L 33/21* (2016.08); *A61K 8/73* (2013.01); *A61Q 19/00* (2013.01); *A23V 2002/00* (2013.01); *A61K 2800/10* (2013.01); *A61K 2800/49* (2013.01); *A61K 2800/592* (2013.01)

(58) Field of Classification Search
CPC ........ A23L 1/308; A23L 33/115; A23L 33/21; A23L 33/20; A23L 27/60; A23L 7/117; A23L 29/273; A61K 8/986; A61K 8/73; A23D 7/005; A21D 2/18; A21D 2/183; A23G 3/42; A23C 9/137; A61Q 19/00
See application file for complete search history.

(56) References Cited

U.S. PATENT DOCUMENTS

| 5,169,671 | A | 12/1992 | Harada et al. |
| 5,702,942 | A | 12/1997 | Leathers et al. |
| 6,602,994 | B1 * | 8/2003 | Cash ...................... A61K 8/027 536/100 |
| 2005/0059633 | A1 * | 3/2005 | Van Geel-Schuten .................... C12N 9/1051 514/54 |
| 2006/0093720 | A1 | 5/2006 | Tatz |
| 2006/0127328 | A1 | 6/2006 | Monsan et al. |
| 2006/0166336 | A1 | 7/2006 | Leathers et al. |

FOREIGN PATENT DOCUMENTS

| WO | WO 2000/047628 A2 | 8/2000 |
| WO | WO 2000/047727 A2 | 8/2000 |
| WO | WO 2003/008618 A2 | 1/2003 |
| WO | WO 2004/023894 A1 | 3/2004 |
| WO | WO 2005/089483 A2 | 9/2005 |
| WO | WO 2006/088884 A1 | 8/2006 |
| WO | WO 2007/128559 A2 | 11/2007 |
| WO | WO 2008/051760 A2 | 2/2008 |
| WO | WO 2008/098975 A1 | 8/2008 |
| WO | WO 2010/043423 A1 | 4/2010 |

OTHER PUBLICATIONS

Of Food Processing—The Yin and Yang of Emulsifiers; published in 2004.*
Cote and Robyte, Carbohydrate Research, vol. 101, pp. 57-74 (1982).
Cote, Carbohydrate Polymers, vol. 19, pp. 249-252 (1992).
European Search Report from EP 12169201.6-2114 dated Jul. 20, 2012.
First Office Action of Chinese Patent Application No. 201310247564.0 dated Apr. 11, 2014—English translation and Chinese Office Action, 6 pages.

(Continued)

Primary Examiner — Sarah Pihonak
Assistant Examiner — Jason Deck
(74) Attorney, Agent, or Firm — Arent Fox LLP

(57) ABSTRACT

The invention is directed to the use of alternan as texturizing agent, particularly as fat or oil replacer in foodstuffs or cosmetic preparations, a homogeneous composition comprising alternan and water, the use of the homogeneous composition as texturizing agent in foodstuffs or cosmetic preparations, and foodstuffs and cosmetic preparations comprising alternan as texturizing agent or a homogeneous composition comprising alternan.

10 Claims, No Drawings

(56) References Cited

OTHER PUBLICATIONS

Hardin, B. Agriculture Research, pp. 10-11 (1999) XP002486611.
Horn et al., Applied Microbiology and Biotechnology, vol. 46, pp. 524-532 (1996).
International Search Report for International Patent Application No. PCT/EP2009/001760 dated Oct. 6, 2009.
Jeanes et al., Journal of America Chemical Society, vol. 76, pp. 5041-5052 (1954).
Kuntz, Food Product Design, retrieved from the Internet at http://www.foodproductdesign.com/articles/463/463_1299ap.html (1999) XP002492224.
Misaki et al., Carbohydrate Research, vol. 84, pp. 273-285 (1980).
Seymour et al., Carbohydrate Research, vol. 74, pp. 41-62 (1979).
Written Opinion for International Patent Application No. PCT/EP2009/001760 dated Oct. 6, 2009.

\* cited by examiner

USE OF ALTERNAN AS TEXTURIZING AGENT IN FOODSTUFFS AND COSMETICS

CROSS REFERENCE TO RELATED APPLICATION

This application is a Divisional application Ser. No. 12/921,046 filed Nov. 18, 2010, which claims priority to U.S.C. 371 National Phase of PCT Application No. PCT/EP2009/001760 filed Mar. 6, 2009, the disclosure of these prior applications are hereby incorporated in their entirety by reference.

The present invention is directed to the use of alternan as texturizing agent, particularly as fat or oil replacer in foodstuffs or cosmetic preparations, a homogeneous composition comprising alternan and water, the use of the homogeneous composition as texturizing agent in foodstuffs or cosmetic preparations, and foodstuffs and cosmetic preparations comprising alternan as texturizing agent or a homogeneous composition comprising alternan.

In recent years, problems of obesity and hyperlipemia have increased due to excessive consumption of oils, fats, sugars, etc., and decreased consumption of dietary fibers. It has been suggested that certain adult diseases, which are leading causes of death, such as cancer, heart diseases, etc., are associated with excessive consumption of oils, fats, and sugars and decreased consumption of dietary fibers. For these reasons, low calorie foodstuffs wherein oil or fat is replaced by substances with beneficial texturizing properties have become popular.

Some Polysaccharides have been described as texturizing agents and fat replacers. U.S. Pat. No. 5,169,671 relates to a food or drink containing a fructose polymer mainly composed of beta-2,1-bond, referred to as "polyfructan", as a substitute for oils, fats, and sugars and having improved gel properties compared with foods containing other oil, fat, or sugar substitutes and a creamy taste and texture equivalent to that derived from oils and fats and a method of producing such a food or drink.

WO2007/128559 and WO2007/128559 teach that very long chain inulins are efficient texturizing agents and fat replacers, especially in dairy products and ice cream.

However, in view of the increased need for efficient texturizing agents and fat replacers for foods it was an object of the present invention to find alternative substances which can be used for this purpose The present invention is directed to the use of alternan as a texturizing agent in foodstuffs or cosmetic preparations.

In another aspect the present invention is directed to the use of alternan as an emulsifier, preferably for foodstuffs and cosmetic preparations.

A texturizing agent according to the present invention imparts texture to foodstuffs or cosmetic preparations or modifies the texture of foodstuffs or cosmetic preparations. The term "texture" refers to the properties held and sensations caused by the external surface of foodstuffs or cosmetic preparations received through the sense of touch.

In connection with foodstuffs, the term "mouthfeel" is used alternatively to the term "texture" and both terms are used herein interchangeably with respect to foodstuffs. In connection with cosmetic preparations, a major meaning of the term texture is the skin feel of a cosmetic preparation.

In the present invention it can be shown that alternan is a very suitable fat or oil replacer in foodstuffs. The fat or oil component of foodstuffs has usually a major impact on its texture/mouthfeel, organoleptic characteristics, and flavor. A fat or oil content usually imparts a creamy and smooth mouthfeel to a foodstuff. These desired properties of foodstuffs can also be reached by adding alternan to foodstuffs. The term "fat or oil replacer" in this connection means that at least a part of a fat or oil component in a foodstuff is removed from the foodstuff and replaced by alternan. The term "fat or oil replacer", however, can also mean that the total fat or oil component in a foodstuff is removed from the foodstuff and replaced by alternan.

Alternan is a polysaccharide composed of glucose units. The glucose units are linked to each other via a-1,3- and a-1,6-glycosidic bonds, and said two types of bonds predominantly appear alternatingly. Alternan may contain branches (Seymour et al., Carbohydrate Research 74, (1979), 41-62). Alternan and methods for producing alternan are well known from the state of the art. See for example Jeanes et al. (1954) J. Am. Chem. Soc., 76: 5041-5052, Misaki et al. (1980) Carbohydr. Res., 84: 273-285, Cote and Robyt (1982), Carbohydr. Res., 101: 57-74, Cote (1992), Carbohydrate Polymers 19, 249-252, WO 00/47727, U.S. Pat. No. 5,702,942, US20060127328, PCT/EP2008/051760.

Alternan according to the present invention preferably has a weight average molecular weight Mw in the range of 10 000 000 g/mol to 60 000 000 g/mol (determined with GPC MALLS), more preferably in the range of 12 000 000 g/mol to 50 000 000 g/mol. In a special embodiment, alternan is produced with alternansucrase originating from Leuconostoc Mesenteroides as described in WO 00/47727 and shows a weight average molecular weight Mw in the range of 33 000 000 g/mol to 60 000 000 g/mol (determined with GPC MALLS), more preferably in the range of 33 000 000 g/mol to 50 000 000 g/mol. In still another special embodiment, alternan is produced with truncated alternansucrase enzyme as described in PCT/EP2008/051760 and shows a weight average molecular weight Mw in the range of 12 000 000 g/mol to 30 000 000 g/mol (GPC MALLS), more preferably in the range of 14 000 000 g/mol to 28 000 000 g/mol, still more preferably in the range of 16 000 000 g/mol to 26 000 000 g/mol, most preferably 19 000 000 g/mol to 23 000 000 g/mol. Truncated alternansucrase enzymes, methods for producing alternan therefrom as well as the alternan itself are described in PCT/EP2008/051760, which is incorporated herein by reference in its entirety.

A preferred foodstuff wherein alteman is used as a fat replacer is selected from dairy products, yoghurts, ice creams, milk-based soft ice, milk-based garnishes, puddings, cream, whipped cream, chocolate cream, butter cream, crème fraiche, curd, milk, such as skim milk, buttermilk, soured milk, kefir, milkshakes, egg custard, cheese, such as cream cheese, soft cheese, sliced cheese, hard cheese, nutrition bars, energy bars, breakfast bars, confectionery, bakery products, crackers, cookies, biscuits, cereal chips, snack products, diet drinks, finished drinks, sports drinks, stamina drinks, powdered drink mixtures for dietary supplementation, infant and baby foodstuff, bread, croissants, breakfast cereals, spreads, sugar-free biscuits and chocolates, calcium chews, meat products, sausages, mayonnaise, dressings, nut butter, deep-frozen meals, sauces, gravy, soups, shortenings, canned foods and ready-to-serve meals.

The level of alternan in the foodstuff depends on the kind of foodstuff. Usually, alteran is used in an amount which is sufficient to reach the desired degree of fat/oil replacement and the desired mouthfeel properties. Without limitation exemplary levels of alteman in foodstuffs are 0.1-10 weight percent, more preferably 0.1-5 weight percent, and most preferably 0.1-3 weight percent, based on the total weight of all components forming the foodstuff.

Oils and fats may be wholly substituted with alternan. However, a preferred degree of substitution is 20 to 80% by weight based on weight of the oils and/or fats.

In a further aspect the present invention is directed to a foodstuff comprising alternan as texturizing agent, particularly as a fat or oil replacer. The foodstuff is preferably selected from the above mentioned foodstuffs The term "foodstuff" according to the invention also encompasses beverages.

The present invention is also directed to a cosmetic preparation, comprising alternan as texturizing agent. The cosmetic preparation where alternan may be employed include, but are not limited to, deodorants, antiperspirants, antiperspirant/deodorants, shaving products, skin creams and lotions, moisturizers, toners, bath products, cleansing products, hair care products such as shampoos, conditioners, mousses, styling gels, nails creams and lotions, cuticle softeners, protective creams such as sunscreen, anti-aging products, and other personal care formulations.

In a further aspect, the present invention is directed to a homogeneous composition comprising alternan and water. The term "homogeneous composition" means that the composition shows no visible phase separation or separation of its constituents (not visible to the naked eye).

Depending on the relative amounts of alternan and water, said homogeneous composition can show a wide viscosity range. So, the homogeneous composition may be a liquid or a more viscous cream, wherein a cream is preferred.

In one embodiment the composition according to the invention comprises 5-15 weight-% alternan and 85-95 weight-% water, based on the total weight of the composition, more preferably 8-13 weight-% alternan and 87-92 weight-% water. Further components may be included, such as surfactants and salts.

In another embodiment, a homogeneous composition according to the invention comprises alternan, water and at least one fat or oil or a mixture of fat(s) and oil(s). Said homogeneous composition comprising alternan, water and at least one fat and/or oil shows no visible phase separation between the fat or oil component and the water component (not visible to the naked eye). Thus, said composition comprising alternan, water and at least one fat and/or oil may also be designated as an emulsion.

Depending on the relative amounts of alternan, water, and oil and/or fat, said homogeneous composition can show a wide viscosity range. So, the homogeneous composition may be a liquid or a more viscous cream, wherein a cream is preferred.

In one embodiment a composition comprises 5-15 weight-% alternan, 70-90 weight-% water, 5-15 weight-% fat or oil, more preferably 8-13 weight-% alternan, 74-84 weight-% water, and 8-13 weight-% fat or oil, based on the total weight of the composition. Further components such as surfactants and salts may be included.

Preferred fats/oils as a component for a homogeneous composition comprising alternan, water and at least one fat and/or oil are selected from arachidic oil, avocado oil, cotton seed oil, safflower oil, peanut oil, hazelnut oil, hemp oil, jojobaoil, camenillia oil, cocoa butter, coconut oil, pumpkin oil, linseed oil, macadamia nut oil, corn germ oil, almond oil, mango seed fat, poppy seed oil, evening primrose oil, olive oil, palm oil, palm kernel oil, papaya oil, pistachio nut oil, pecan nut oil, rapeseed oil, castor oil, mustard seed oil, sesame oil, rhea butter, soybean oil, sunflower oil, walnut oil, water melonseed oil, grapeseed oil, wheat germ oil, cedarwood oil, wherein said oils might optionally be hardened oils.

In still another aspect, the present invention is directed to a homogeneous composition comprising alternan and milk. In a preferred embodiment said composition comprises 5-15 weight-% alternan and 85-95 weight-% milk, based on the total weight of the composition, more preferably 8-13 weight-% alternan and 87-92 weight-% milk. Further components may be included, such as surfactants and salts. A cream comprising alternan and milk might preferably be used for all kind of dairy products.

The viscosity of a homogeneous composition according to the invention is adapted to the desired kind of foodstuff or cosmetic preparation, i.e. to the desired final viscosity of said foodstuff or cosmetic. However, as said above, the homogeneous composition is preferably a cream, wherein a preferred range of viscosity of a cream is from 0.5 to 1.5 Pa*s, more preferably 0.8 to 1.3 Pa*s at 20° C. and a shear rate of 40 $s^{-1}$.

All of the above described homogeneous compositions, preferably creams, are hereinafter also designated as "(homogeneous) composition according to the invention" or "cream according to the invention".

The present invention also relates to a method for preparing the above described compositions, the method comprising
 a) giving alternan and water into a vessel
 b) applying shear to obtain a homogeneous composition, and optionally
 c) adding oil or fat and applying shear to obtain a homogeneous composition.

The optional step c) relates to the above described embodiment of a homogeneous composition, comprising alteman, water and oil or fat.

Mixing in steps b) and c) is preferably done under high shear with commonly known devices for such purpose, such as ULTRA TURRAX® dispersing tool from IKA company. In a preferred embodiment, steps a) and b) are performed simultaneously, e.g. by adding alteman as a powder to water with simultaneous application of high shear. Optional components as salts and emulsifiers might be added at any stage of the preparation.

In a further aspect, the present invention is related to the use of a homogeneous composition as described above for the manufacture of foodstuffs or cosmetic preparations. In this connection, said homogeneous compositions, preferably creams, can preferably used for above-listed foodstuffs and cosmetics.

According to the present invention the homogeneous compositions can be used as constituent for foodstuffs or cosmetic preparations. In this connection, homogeneous compositions according to the present invention can fulfill, without limitation, following functions: giving body to foodstuffs or cosmetic preparations, act as a base for foodstuffs or cosmetic preparations, act as a texturizing agent for foodstuffs or cosmetic preparations. The homogeneous compositions according to the present invention can fulfill one or more of the aforementioned functions.

In regard to texturizing properties the homogeneous compositions according to the present invention are preferably used as a fat or oil replacer in foodstuffs. In this connection, the homogeneous composition is preferably a cream. The preferred foodstuffs for said use are selected from dairy products, yoghurts, ice creams, milk-based soft ice, milk-based garnishes, puddings, cream, whipped cream, chocolate cream, butter cream, crème fraiche, curd, milkshakes, egg custard, cheese, such as cream cheese, soft cheese, sliced cheese, hard cheese, nutrition bars, energy bars, breakfast bars, confectionery, bakery products, crackers, cookies, biscuits, cereal chips, snack products, infant and baby foodstuff, bread, croissants, spreads, sugar-free biscuits and chocolates, calcium chews, meat products, sausages, mayonnaise, dressings, nut butter, deep-frozen meals, sauces, gravy, soups, shortenings, canned foods and ready-to-serve meals.

Homogeneous compositions according to the invention have a texture similar to oils or fats. By substituting this composition for liquid oils and solid fats, for example in dressings, mayonnaise, fresh cream, cream cheese, butter, salad oil, etc., in various cooked and processed food, the number of calories in the resulting food are greatly reduced. Oils and fats may be wholly substituted with a homogeneous composition according to the present invention. However, a preferred degree of substitution is 20 to 80% by weight based on the oils and fats.

Finally, the present invention is also directed to a foodstuff or cosmetic preparation, characterized in that during its manufacturing process a homogeneous composition according to the present invention was added as a constituent. In the foodstuff or cosmetic, a homogeneous composition according to the present invention preferably fulfills the functions as described above with respect to its use. Depending on the kind of foodstuff or cosmetic and its manufacturing process, the homogeneous composition might be present in the final product without substantial structural alteration. This might for example be the case when a cream of the invention is used as the base for a cosmetic preparation and only some active ingredients are added. In such case, the final foodstuff or cosmetic preparation is characterized in that it still comprises the cream. In other cases, e.g. in products which are heat treated after addition of the cream, the cream might be subjected to major alterations in its structure. The present invention is to be understood to encompass all foodstuffs and cosmetic preparations during whose manufacturing process a cream according to the invention was added, regardless of whether the initial structure of the cream is altered in the final product or not.

In the following section, the present invention is further illustrated by examples, which are, however, not intended to limit the scope of the invention as defined in the appended claims.

EXAMPLES

1. Manufacture of Alternan

Plasmid pAI-B-AlSu Q29 was transformed in *E. coli* DH5a. Vector pAI-B-AlSu contains the full-length coding sequence of alternansucrase derived from Leuconostoc mesenteroides strain NRRL B-1355 (cf. WO 00/47727), lacking the N-terminal 39 amino acids from the signal peptide, fused to an octapeptide strep-tag at the C-terminal end. The strep-tag is linked to the protein through a dipeptide linker. Expression of alternansucrase is under the transcriptional control of the tetA promoter/operator and repressor. The tetA promoter is tightly regulated by the tet repressor which is encoded on the same plasmid and is constitutively expressed from the β-lactamase promoter. In this way, expression of alternansucrase is stringently repressed until efficient chemical induction by tetracycline or anhydrotetracycline, AHT.

The cells were pre-cultured in mineralmedium (Horn et al., 1996) with 100 µg/ml Ampicillin and 10% LB medium. Mineralmedium, without LB, was inoculated with this pre-culture. The cells were grown at 37° C., induced with Anhydrotetracyclin (AHT) (0.2 mg/L), and grown further at 25° C. The cells were harvested, resuspended in [10 mM MOPS pH 7.6; 2.5 mM CaCl2 and 0.05% Trition X-100] and extracted with a high pressure homogenisator. The cell lysate was centrifuged at 20 000 rpm for 20 minutes at 4° C. The supernatant was filtered over a 0.22 µm filter.

Alternan was produced in a 60 L Biotransformation containing 0.13% Acetic Acid, 100 mM NaAc pH5.3, 20% Sucrose, 1 mM DTT, 1600 ml filtered protein extract (ca. 3900 Units). The reaction mixture was incubated for 60 h. at 37° C. The polymer was precipitated with 60 L Technical Ethanol 40 h 4° C., washed 2× with 60 L 60% Technical Ethanol, and 1× with 60 L 60% Ethanol Absolute. The product was dried through lyophilization Reference:

Horn U, Strittmatter W, Krebber A, Knupfer U, Kujau M, Wenderoth R, Muller K, Matzku S, Pluckthun A, Riesenberg D. High volumetric yields of functional dimeric miniantibodies in *Escherichia coli*, using an optimized expression vector and high-cell-density fermentation under non-limited growth conditions. Appl Microbiol Biotechnol 1996; (46): 524-532.

2. Application Tests 2.1 Mayonnaise

Background:

The objective was to test the alternan as produced in example 1 (hereinafter "altenan") as a fat replacer in a model mayonnaise type dressing system. A model mayonnaise dressing was developed with the control mayonnaise at 68% oil (the standard of identity for mayonnaise is >65% oil).

Three methods of incorporating the alternan were evaluated:

1. Making an alternan cream and adding it in the last step after the oil.
2. Dry blending the alternan with dry ingredients and adding it to the egg mixture.
3. Making an alternan cream and adding it to the egg mixture.

After the initial experiments using Test Method 1, it was determined that the level of alternan needed to be higher. Fat replacement levels of 25% to 50% were tested.

Control Formula and Method:

| Ingredients | % |
|---|---|
| Egg Mixture | |
| Egg Yolks | 11.15 |
| Water | 9.17 |
| Vinegar (Distilled White, 5% Acidity) | 8.78 |
| Sugar | 1.30 |
| Salt | 0.81 |
| Mustard Powder | 0.64 |
| Mayonnaise | |
| Egg Mixture (from above) | 31.85 |
| Salad Oil (Soybean) | 68.15 |

The egg yolks, water, vinegar (5% acidity), sugar, salt and dry mustard were mixed together and heated slowly until just beginning to boil.

The egg mixture was allowed to cool slightly and then soybean oil was sheared into the mixture using a Silverson High Shear mixer fitted with a Square Hole High Shear screen to form an emulsion.

The mayonnaise was refrigerated overnight before measuring the viscosity (sample temperatures ranged from 3.3 to 6.7° C.). Viscosity was measured with a Brookfield RV at Speed 10 with Spindle #5 or 6, the reading was recorded after 1 minute.

Test Method 1:

| Ingredients | | |
|---|---|---|
| Alternan Cream | | % |
| Water | | 80.91 |
| alternan | | 10.0 |
| Salad Oil (Soybean) | | 9.09 |
| Mayonnaise | 50% Fat Repl. | 25% Fat Repl. |
| Egg Mixture (as described in Control) | 31.85 | 31.85 |
| Salad Oil (Soybean) | 34.15 | 50.15 |
| Alternan Cream | 34.00 | 18.00 |

Final % of alternan in 50% Fat Replaced Mayonnaise = 3.4%
Final % of alternan in 25% Fat Replaced Mayonnaise = 1.8%

A cream was prepared with water, 10% of the alternan and 9.09% Soybean Oil (using the Silverson High Shear mixer).

The mayonnaise was prepared as described in the Control method but after the addition of the Soybean Oil, the alternan Cream was sheared in.

"Blank"

A sample with a 25% reduction in oil was prepared by simply increasing the water (no alternan cream was added).

Results and Observations, Test Method 1:

The formula and process for preparing the alternan cream worked well. The cream was white with a medium viscosity. However, the dressings prepared with the alteman cream were much thinner than the control. The test product with a 25% reduction in oil had some viscosity and was similar to a pourable style dressing. The Test product with a 50% reduction in oil was very thin. The level of alternan may have been too low.

| Sample | pH | Aw | Viscosity (centapoise)* | Observations |
|---|---|---|---|---|
| Control | 4.09 | 0.964 | 33,000 | Thick, forms "peaks" |
| Test with alternan, 50% oil replacement | 4.27 | 0.984 | 5,500 | Thin |
| Test with alternan, 25% replacement | 4.24 | 0.978 | 9,500 | Some thickness/ slight gel |
| Test, Blank with 25% replacement | 4.27 | 0.982 | 6,200 | Some thickness/ slight gel |

Test Method 2:

The alternan powder was dry blended with the sugar, salt and mustard. The Control procedure was then followed. A 50% reduction in fat was tested using 10% alternan and 5% alteman. The amount of water in the formula was adjusted to compensate for the reduction in oil and the addition of the alternan to balance the formula to 100%.

Results and Observations, Test Method 2:

The 10% level of alternan was too high for this application. It was very difficult to incorporate the alternan into the egg mixture and a foodstuff processor to mix the mayonnaise had to be used. The resulting product was more like a shortening or spread than a spoonable dressing. The 5% level worked well with the method as described and the resulting product was similar to Control with respect to appearance, texture and viscosity.

| Sample | pH | Viscosity (centapoise) | Observations |
|---|---|---|---|
| Control (same as described in Method 1) | 4.09 | 33,000 | Thick, forms "peaks" |
| 50% Reduced Fat with 10% alternan | | 1,060,000* | Similar to shortening or butter, fairly stiff and slightly gel like with a smooth/fatty feel. Oil droplets are very small and uniform (microscopic examination). |
| 50% Reduced Fat with 5% alternan, Sample 1 | | 39,700 | Thick, similar to control mayonnaise. Has a smooth, fatty feel when rubbed between the fingers. Very small and uniform oil droplets (microscopic examination). |
| 50% Reduced Fat with 5% alternan, Sample 2 | 4.14 | 22,000 | Thinner than the control but still like a mayonnaise. Very fine and uniform oil droplets (microscopic examination). |

*Since the sample was so thick the viscosity measurement procedure was modified: the Brookfield with Heliopath Spindle F was used at speed 5.

Test Method 3

| Ingredients | |
|---|---|
| | % |
| Egg Mixture | |
| Egg Yolks | 11.15 |
| Water | 0 |
| Vinegar (Distilled White, 5% Acidity) | 8.78 |
| Alternan Cream* | 48.25 |
| Sugar | 1.30 |
| Salt | 0.81 |
| Mustard Powder | 0.64 |
| *Alternan Cream | |
| Water | 79.30 |
| alternan | 10.36 |
| Salad Oil (Soybean) | 10.34 |
| Mayonnaise | |
| Egg Mixture | 70.93 |
| Salad Oil (Soybean) | 29.07 |

Final level of alternan = 5%

Alteman Cream

Add the alternan into the water slowly while shearing with the Silverson mixer.

After all the alternan is incorporated, add the oil slowly until well blended.

Follow the control procedure for the egg mixture but whisk the alternan Cream in last.

Follow the control procedure for preparing the mayonnaise.

Results and Observations, Test Method 3:

The method worked well to prepare the alternan cream and it blended into the egg mixture easily. The egg mixture was thick but flowable. The finished mayonnaise was thicker than the control.

| Sample | pH | Viscosity (centapoise) | Observations |
|---|---|---|---|
| Control, 2$^{nd}$ Sample | 4.16 | 35,700 | Thick, typical mayonnaise. Oil droplets are mostly very small with a few larger ones (microscopic examination). |
| 50% Reduced Fat with 5% alternan | 4.17 | 68,000 | Thicker than the control but still like a mayonnaise. Oil droplets look the same as control (microscopic examination). |

Discussion and Conclusions:

The alternan works well to replace 50% of the fat in a spoonable dressing/mayonnaise system at a 5.0% level. A lower level (3.4%) did not add enough viscosity to be comparable to the control. At the 5.0% level, a fairly large variation in the sample viscosity was found when producing a replicate sample on a different date and when using an alternate method. When the alternan was dry blended with other dry ingredients and then added to the egg mixture, resulting viscosities were 39,700 cps and 22,000 cps. However, when the alternan was first made into a cream and then incorporated into the egg mixture the resulting product viscosity was 68,000 cps.

2.2 Pourable Dressing

Background:

The objective was to test the carbohydrate as a fat replacer in a model pourable dressing system. We initially tested a 50% reduction in fat and tested several oil types. We later tested a further reduction in fat with one oil type. The reference material selected was Avicel (FMC BioPolymers, microcrystalline cellulose and carboxymethyl cellulose), a carbohydrate commonly used in low and no fat salad dressings.

Methods:

| Ingredients | Control % | Test with alternan % | Reference % |
|---|---|---|---|
| Water | 21.35 | 38.85 | 42.6 |
| Xanthan Gum | 0.25 | 0.25 | 0.25 |
| Propylene Glycol Alginate | 0.15 | 0.15 | 0.15 |
| alternan | 0.00 | 5.00 | 0.00 |
| Avicel SD 3410 | 0.00 | 0.00 | 1.25 |
| Salt | 1.75 | 1.75 | 1.75 |
| High Fructose Corn Syrup | 21.0 | 21.0 | 21.0 |
| Vinegar (120 grain) | 10.5 | 10.5 | 10.5 |
| Vegetable Oil | 45.00 | 22.5 | 22.5 |

Dry blend the gums (and alternan or Avicel) and add them to the water while shearing with the Silverson High Shear mixer.

Shear for 5 minutes. Add the salt, HFCS and vinegar and mix.

Slowly add the oil while shearing and shear for an additional 1.5 minutes after all the oil is added.

Note: a "blank" dressing was also prepared with 50% reduced oil but no alternan or avicel in order to determine the viscosity contribution of the xanthan and PGA gums. The Avicel was tested at 0.5, 1.0 and 1.25% but the highest level was closest in viscosity to the control (still lower). An additional sample was also prepared as a reference in which the two gums were increased to levels recommended for a dressing of approximately 20% oil (0.40% xanthan gum and 0.25% PGA).

Results and Observations, Oil Comparison:

The following table summarizes the results for all the oils tested

| Variable | Cold* Viscosity (cps) | Ambient** Viscosity (cps) | pH | Aroma (Ambient) | Observations and Microscopic Evaluation |
|---|---|---|---|---|---|
| Control with 45% Soybean Oil, | 15,200 | 13,200 | 3.51 | Oily, slightly painty, pungent vinegar. | Pale yellow/beige color, no separation. Fairly uniform oil droplets, range about 20 to 30 microns. |
| Control with 45% Soybean Oil, | 14,000 | 11,040 | 3.50 | Oily, slightly painty, pungent vinegar. | Pale yellow/beige color, no separation. Fairly uniform oil droplets, range about 20 to 30 microns. |
| Test with 22.5% Soybean Oil, | 12,880 | 9,200 | 3.54 | Mild, slightly oily, slight painty, low pungent. | Whiter/brighter than control, no separation. Small to medium oil droplets in the range of 2 to 20 microns. |
| Test with 22.5% Soybean Oil, | 13,400 | 8,800 | 3.55 | Mild, slightly oily, slight painty, low pungent. | Whiter/brighter than control, no separation. Fairly uniform oil droplets, most roughly 6 to 10 microns. |
| Test with 22.5% Corn Oil | 13,320 | 9,200 | 3.54 | Very mild, little to no pungency. | Slightly more beige versus the control, no separation. Small to medium droplets in the range of 2 to 20 microns. |
| Test with 22.5% Canola Oil (Rapeseed) | 13,680 | 9,600 | 3.54 | Mild, slightly floral, very slight pungent. | Slightly darker/more tan than control, no separation. Small to medium oil droplets in the range of 2 to 20 microns. |
| Test with 22.5% Sunflower Oil | 12,600 | 9,200 | 3.55 | Mild, slightly nutty, very low pungent. | Slightly whiter than the control, no separation. Small to medium oil droplets in the range of 2 to 20 microns. |
| Test with 22.5% Extra Virgin Olive Oil | 14,280 | 9,200 | 3.57 | Fruity oil, no pungency. | Greenish/yellow color compared to the control, no separation. Small to medium oil droplets in the range of 2 to 20 microns. |

| Variable | Cold* Viscosity (cps) | Ambient** Viscosity (cps) | pH | Aroma (Ambient) | Observations and Microscopic Evaluation |
|---|---|---|---|---|---|
| Test "Blank" with 22.5% Soybean Oil | 3,440 | 2,720 | 3.42 | Oily, slightly painty, mild pungency. | Slightly whiter/brighter than control, no separation. Oil droplets not uniform, in the range of 5 to >40 microns. |
| Reference with 22.5% Soybean Oil, Increased Xanthan and PGA Gums | 7,440 | 6,400 | 3.54 | Oily, slightly painty, mild pungency. | Slightly whiter than the control, no separation. Small to medium oil droplets in the range of 2 to 20 microns. |
| Reference with 22.5% Soybean Oil, 1.25% Avicel SD 3410 | 7,720 | 6,320 | 3.67 | Moderate oil, slightly painty, some pungency. | Slightly more white versus the control, no separation. Oil droplets in the range of 2 to 30 microns. |
| Control with 45% Tuna Oil | 11,200 | 6,320 | 3.49 | Very fishy. | Some separation noted, 3-5 mm of clear liquid on top, the color is more opaque on the bottom. Oil droplets are not uniform. Size range is about 2 to 100 microns. |
| Test with 22.5% Tuna Oil | 15,880 | 8,600 | 3.53 | Somewhat fishy, not pungent. | No separation noted but a slight oil "slick" on the top. Oil droplets are more uniform and smaller versus the control. Most are about 2 to 30 microns, some larger. |
| Reference with 22.5% Tuna Oil, 1.25% Avicel SD 3410 | 9,800 | 6,280 | 3.62 | Somewhat fishy, not pungent. | No separation noted but a slight oil "slick" on the top. Oil droplets are in the range about 2 to 50 microns, some larger, many elongated versus round. |

*Cold Viscosity: Measured on samples immediately after removing from the refrigerator (range 3.3 to 5.6° C.).
**Ambient Viscosity: Measured on samples at room temperature (range 20 to 20.6° C.).

Stability Study

Several of the samples were tested for stability by putting them at 37.8° C. and evaluating them at 3 and 7 days. Note that the Tuna Oil samples were not produced in time to include them in the study.

The following table summarizes the results of the stability test:

| Sample | "Initial" Viscosity Sample shaken | Day 3 Viscosity Equilibrated sample, not shaken | Day 3 Viscosity Sample shaken | Day 3 Observations | Day 7 Viscosity Equilibrated sample, not shaken, | Day 7 Viscosity Sample shaken | Day 7 Observations |
|---|---|---|---|---|---|---|---|
| Control | 12,960 | 13,480 | 12,080 | No separation, color similar, oil droplets in the range of 20 to 40 microns. | 12,880 | 10,520 | Same as Day 3 |
| Test with Soybean Oil | 8,880 | 12,680 | 9,360 | No separation, color similar, oil droplets in the range of 2 to 20 microns. | 12,680 | 9,200 | About ¼" of clear liquid noted on the bottom of the jar. Oil droplets look the same as Day 3. |
| Test with Corn Oil | 9,000 | 12,280 | 9,200 | No separation, color similar, oil droplets in the range of 2 to 20 microns. | 11,760 | 8,760 | About ¼" of clear liquid noted on the bottom of the jar. Oil droplets look the same as Day 3. |
| Test with Canola Oil | 9,520 | 13,040 | 9,680 | No separation, color similar, oil droplets in the range of 2 to 20 microns. | 12,080 | 9,000 | About ¼" of clear liquid noted on the bottom of the jar. Oil droplets look the same as Day 3. |

| Sample | "Initial" Viscosity Sample shaken | Day 3 Viscosity Equilibrated sample, not shaken | Day 3 Viscosity Sample shaken | Day 3 Observations | Day 7 Viscosity Equilibrated sample, not shaken, | Day 7 Viscosity Sample shaken | Day 7 Observations |
|---|---|---|---|---|---|---|---|
| Test with Sunflower Oil | 9,320 | 13,080 | 9,400 | No separation, color similar, oil droplets in the range of 2 to 20 microns. | 12,160 | 9,200 | About ¼" of clear liquid noted on the bottom of the jar. Oil droplets look the same as Day 3. |
| Test with Olive Oil | 9,480 | 12,800 | 9,920 | No separation, color slightly browner, oil droplets in the range of 2 to 20 microns. | 13,000 | 9,440 | About ¼" of clear liquid noted on the bottom of the jar. Oil droplets look the same as Day 3. |
| Reference with Increased Gums | 6,560 | 7,080 | 6,000 | No separation, color similar, oil droplets in the range of 2 to 20 microns. | 6,480 | 5,600 | Same as Day 3 (no separation noted). |
| Reference with 1.25% Avicel | 6,600 | 8,480 | 6,800 | No separation, color similar, oil droplets in the range of 2 to 20 microns. can see "fibers" under microscope. | 8,200 | 6,800 | No separation noted. Most oil droplets in the range of 2 to 20 microns, some up to 40 microns. |

Further Reduced Fat Dressing

In order to determine if the alternan would work in further reducing the fat in the salad dressing, samples with 10% fat (reduced from 45%) were prepared. At 10% fat, the salad dressing would qualify for a low fat claim which is ≤3.0 grams of fat per serving, serving size is 30 grams. Two higher levels of alternan were tested: 6.5% and 7.75% (7.75% was tested first and the sample was thicker than the control). The samples were prepared as described previously. After preparation, the samples were refrigerated overnight and measured for viscosity. The samples were then allowed to come to ambient temperature and viscosity was checked again. We then put the samples at 37.8° C. to test stability and evaluated at 3 and 7 days A table summarizing the results follows:

Discussion:

The alternan works well to partially replace the fat in a reduced fat salad dressing. The alternan acts to build back the viscosity which is lost when the oil is decreased. The appearance and aroma of the test dressings was fairly comparable to the Control and the alternan may act to mask some of the pungent aroma. There didn't seem to be an interaction between the alternan and the oil type. The thickness of the dressing seemed to be related to the iodine value of the oil used, the lower the iodine value, the less double bonds, the thicker it would tend to be at refrigerated conditions. There did seem to be a slight advantage to using the alternan in a fish oil containing dressing. The control dressing separated and the oil droplets were larger versus the test dressing with alternan which did not separate and had

| Sample Description | pH | Refrig. Viscosity | Ambient Viscosity | Day 3 Viscosity Equilibrated | Day 3 Viscosity Shaken | Day 7 Viscosity Equilibrated | Day 7 Viscosity Shaken | Observations |
|---|---|---|---|---|---|---|---|---|
| 10% SBO, 7.75% alternan | 3.58 | 32,320 | 26,400 | 33,000 | 33,300 | 41,500 | 38,200 | No separation at 3 days, a slight "crack" near top at 7 days. Oil droplets in the range of 2 to 20 microns, most are <10 microns. |
| 10% SBO, 6.5% alternan | 3.58 | 10,520 | 8,120 | 12,800 | 8,640 | 13,080 | 10,200 | No separation at 3 days, a slight amount of clear liquid at the bottom of the jar (about 0.25 cm) at 7 days. Oil droplets in the range of 2 to 20 microns, most are <10 microns. | smaller oil droplets. The alteman containing dressings were able to stand up to some abuse (3 days at 37.8° C.) some separation after 7 days at 37.8° C. was seen. Even though there was some separation, the viscosities remained quite stable. We did note some shear thinning in the Test samples. When samples were allowed to "equilibrate" in a beaker the viscosity was higher versus if the sample was shaken just before the viscosity measurement. We didn't find this to the same extent with the Control dressing. It was possible to reduce the fat in the model dressing to 10% or "low fat" by increasing the alternan to 6.5%. The resulting dressing had similar characteristics to the Control with respect to viscosity and appearance. There was some slight separation after being stored at 37.8° C. for 7 days but the viscosity remained quite consistent.

2.3 Bakery Goods

Background:

The objective was to test the alternan as a fat replacer in bakery goods. Two model systems (cookie and cake) were tested. For cookie the fat replacement was at 30% and for cake at 30% and 50%.

Sugar Snap Cookie

Formula and Methods

| Ingredient | Full fat (g) | % | Test (g) | % |
|---|---|---|---|---|
| Wheat flour standard | 150.0 | 45.4 | 150.0 | 45.4 |
| Water | 25.5 | 7.7 | 35.8 | 10.8 |
| Soda | 1.2 | 0.4 | 1.2 | 0.4 |
| Milk powder | 7.5 | 2.3 | 7.5 | 2.3 |
| Baking powder | 2.3 | 0.7 | 2.3 | 0.7 |
| Salt | 1.5 | 0.5 | 1.5 | 0.5 |
| Shortening | 67.5 | 20.4 | 47.3 | 14.3 |
| Sugar | 75.0 | 22.7 | 75.0 | 22.7 |
| Alternan | — | — | 10.0 | 3.0 |
| sum | 330.5 | 100.0 | 330.5 | 100.0 |
| Fat % | | 21.0 | | 15.0 |
| Fat reduction % | | — | | 30.0 |

Method 1:

a) Full fat cookie (control)

All solids (flour, sugar, soda, baking powder, salt, milk powder) were mixed in farinograph for 30 sec Shortening added and mixed for 1 min and 30 sec Water added and mixed for 2 min and 30 sec Dough rolled (height 1 cm) and 4 cookies cut with a cutter (76.2 mm)

Cookies placed on baking plan and baked at 193° C. for 10 min b) Alternan reduced fat cookie As described in the control except that alternan powder was mixed with solids Method 2:

a) Alternan reduced fat cookie

Making Alternan gel 22% (Alteman powder added to water and sheared with ULTRA TURRAX® at 11600 rpm for 5 min)

All solids (flour, sugar, soda, baking powder, salt, milk powder) were mixed in farinograph for 30 sec Shortening added and mixed for 1 min and 30 sec Alternan gel added and mixed for 2 min and 30 sec Dough rolled (height 1 cm) and 4 cookies cut with a cutter (76.2 mm)

Cookies placed on baking plan and baked at 193° C. for 10 min.

Results and Observations:

| Parameter | | Full Fat | Test 1 | Test 2 |
|---|---|---|---|---|
| Dough weight | g | 326.6 | 326.8 | 324.9 |
| Baked dough | g | 227.6 | 241.5 | 242.9 |
| Dough appearance | | regular | regular | regular-firmly |
| Cookie weight | g | 211.7 | 223.4 | 224.1 |
| Cookie diameter | cm | 8.3 | 7.7 | 7.9 |
| Height of all cookies | cm | 5.0 | 5.3 | 5.4 |
| Cookie volume | cm³ | 270.4 | 246.7 | 264.6 |
| Baking loss | % | 7.0 | 7.5 | 7.7 |
| Spread ratio | | 6.6 | 5.8 | 5.9 |
| Shape | | round | slightly oval | round |
| Browning | | normal | normal | normal |
| Surface | | smooth | coarse | coarse |
| Hardness of cookie | | | | |
| fresh | kg | 3.5 | 5.6 | 7.1 |
| week | kg | 6.1 | 6.2 | 8.6 |
| Crumb moisture | | | | |
| fresh | % | 9.8 | 16.1 | 16.4 |
| week | % | 9.8 | 12.8 | 11.3 |

Test 1 = Cookies with Alternan by method 1
Test 2 = Cookies with Alternan by method 2

Cake (Sand Cake)

Formulas and Methods

| Ingredients | Full fat % | Test 1% | Test 2% | Test 3% | Test 4% | Test 5% |
|---|---|---|---|---|---|---|
| Wheat flour standard | 14 | 14 | 14 | 14 | 14 | 14 |
| Potato starch | 14 | 14 | 14 | 14 | 14 | 14 |
| Shortening | 25 | 17.5 | 12.5 | 12.5 | 12.5 | 12.5 |
| Sugar | 21 | 21 | 21 | 21 | 21 | 21 |
| Vanilla sugar | 1.4 | 1.4 | 1.4 | 1.4 | 1.4 | 1.4 |
| Whole egg | 24 | 24 | 24 | 24 | 24 | 24 |
| Salt | 0.1 | 0.1 | 0.1 | 0.1 | 0.1 | 0.1 |
| Baking powder | 0.5 | 0.5 | 0.5 | 0.5 | 0.5 | 0.5 |
| Alternan | — | 1.5 | 1.5 | 3 | 3 | 6 |
| Water | — | 6 | 11 | 9.5 | 9.5 | 6.5 |
| Sum | 100 | 100 | 100 | 100 | 100 | 100 |
| Fat % | 28 | 20.5 | 15.5 | 15.5 | 15.5 | 15.5 |
| Fat reduction % | | 27 | 45 | 45 | 45 | 45 |

Method 1:

a) Full fat cake (control)

The solids (flour, salt, starch and baking powder were blended (mixture)

The shortening, sugar and vanilla sugar were mixed in a kitchen machine for 1 min The whisked eggs then added and mixed for 1 min The mixture was gradually added and mixed for 2 min 120 g of dough was placed in a baking pan and baked for 40 min at 160° C.

b) Alternan reduced fat cake (Tests 1 to 3 and Test 5)

As described in the control, except that alternan powder was mixed with solids

Method 2:

a) Alternan reduced fat cookie (Test 4)

Making Alternan gel 24% (Alteman powder added to water and sheared with ULTRA TURRAX® at 11600 rpm for 5 min)

The solids (flour, salt, starch and baking powder were blended (mixture)

The Alternan gel, shortening, sugar and vanilla sugar were mixed in a kitchen machine for 1 min.

Results and Observations:

| Parameter | | Full fat | Test 1 | Test 2 | Test 3 | Test 4 | Test 5 |
|---|---|---|---|---|---|---|---|
| Dough consistency | | creamy/firm | less firm | less firm | less firm | less firm | less firm |
| Dough moisture | % | 21.7 | 27.7 | 31.3 | 30.8 | 30.4 | 29 |
| Cake weight | g | 106.9 | 104.4 | 102.7 | 103.2 | 102.9 | 103.6 |
| Baking loss | % | 10.9 | 13 | 14.4 | 14 | 14.25 | 13.7 |
| Cake volume | ml | 575 | 500 | 420 | 420 | 410 | 515 |
| Cake moisture % | % | 12.1 | 16.9 | 19.7 | 19.5 | 18.8 | 17.8 |
| Crumb moisture | % | | | | | | |
| fresh | | 21.1 | 27.3 | 33.6 | 31.4 | 32.2 | 28.4 |
| week | | 12 | 18.1 | 22.5 | 22.2 | 23.2 | 19.1 |
| Cake height | mm | 50.2 | 47.6 | 44.1 | 46.4 | 44.9 | 48.1 |
| Crumb firmness | g | | | | | | |
| fresh | | 337 | 296 | 313 | 285.4 | 319.3 | 213.9 |
| week | | 1282 | 1162 | 1255 | 1170 | 1028 | 1285 |
| Cake browning | | golden brown | golden brown | golden brown | golden brown | golden brown | golden brown |
| Crumb appearance | | succulent/dry (normal) | succulent/less dry | succulent/less dry | succulent/slightly moist | irregularly baked | succulent/less dry |

The invention claimed is:

1. A method of emulsifying a product comprising adding an alternan having a weight average molecular weight (Mw) in the range of 10 000 000 g/mol to 60 000 000 g/mol, as determined with GPC MALLS.

2. The method according to claim 1, wherein the alternan has a weight average molecular weight (Mw) in the range of 33 000 000 g/mol to 60 000 000 g/mol, as determined with GPC MALLS.

3. The method according to claim 1, wherein the alternan has a weight average molecular weight (Mw) in the range of 12 000 000 g/mol to 30 000 000 g/mol, as determined with GPC MALLS.

4. The method according to claim 1, wherein the product is a foodstuff.

5. The method according to claim 4, wherein the foodstuff is a dairy product, yoghurt, ice cream, milk-based soft ice, milk-based garnish, pudding, cream, whipped cream, chocolate cream, butter cream, crème fraiche, curd, milkshakes, egg custard, cheese, nutrition bar, energy bar, breakfast bar, confectionery, bakery product, cracker, cookie, biscuit, cereal chip, snack product, infant and baby foodstuff, bread, croissant, spread, sugar-free biscuit and chocolate, calcium chew, meat product, sausage, mayonnaise, dressing, nut butter, deep-frozen meal, sauce, gravy, soup, shortening, canned food or ready-to-serve meal.

6. The method of claim 5, wherein the cheese is a cream cheese, soft cheese, sliced cheese, or hard cheese.

7. The method according claim 1, wherein the product is a cosmetic preparation.

8. The method according to claim 7, wherein the cosmetic preparation is a deodorant, antiperspirant, antiperspirant/deodorant, shaving product, skin cream and lotion, moisturizer, toner, bath product, cleansing product, hair care product, nail cream and lotion, cuticle softener, protective cream, and other personal care formulations.

9. The method of claim 8, wherein the hair care product is a shampoo, conditioner, mousse, or styling gel.

10. The method of claim 8, wherein the protective cream is a sunscreen or anti-aging product.

* * * * *